United States Patent [19]

Quintanilla Almagro et al.

[11] Patent Number: 5,601,829
[45] Date of Patent: Feb. 11, 1997

[54] PHARMACEUTICAL COMPOSITION OF ACTIVITY IN THE TREATMENT OF COGNITIVE AND/OR NEUROIMMUNE DYSFUNCTIONS

[75] Inventors: Eliseo Quintanilla Almagro; Joaquin Diaz Alperi, both of Alicante, Spain

[73] Assignee: Especialidades Farmaceuticas Centrum, S.A., Spain

[21] Appl. No.: 433,621

[22] Filed: May 3, 1995

[30]     Foreign Application Priority Data

May 6, 1994 [ES] Spain ................................. 94/00957
Feb. 23, 1995 [ES] Spain ................................. 95/00363

[51] Int. Cl.⁶ .................................................. A61K 35/78
[52] U.S. Cl. ........................................ 424/195.1; 514/885
[58] Field of Search ........................... 424/195.1; 514/885

[56]             References Cited

FOREIGN PATENT DOCUMENTS 503208      9/1992   European Pat. Off. .
0503208A1   9/1992   European Pat. Off. ........ A61A 35/78
470204      1/1979   Spain .

*Primary Examiner*—John W. Rollins
*Attorney, Agent, or Firm*—Ostrolenk, Faber, Gerb & Soffen, LLP

[57]              ABSTRACT

A pharmaceutical composition with beneficial effects in disorders which deal with cognitive, neurodegenerative and/or neuroimmune dysfunctions, especially the Alzheimer disease, characterized in that it comprises, as active ingredient, an isolated, natural hydrosoluble extract of the rhizome or leaves of Phlebodium decumanum, Polypodium aureum, Polypodium leucotomos, Polypodium vulgare, Polypodium trisereiale, Pteridium aquilinum, Dryopteris crassirhizoma and Cyathea taiwamiana, and the liposoluble fraction derivates of said extract, together with an acceptable pharmaceutical vehicle.

8 Claims, No Drawings

PHARMACEUTICAL COMPOSITION OF ACTIVITY IN THE TREATMENT OF COGNITIVE AND/OR NEUROIMMUNE DYSFUNCTIONS

This invention refers to a pharmaceutical composition based on natural hydrosoluble extracts of leaves and/or rhizomes of various ferns and/or fractions which are soluble in alcohol, and fractions which are liposoluble in said extracts, the composition of which presents beneficial effects in disorders which deal with cognitive dysfunctions and/or neuroimmunes, especially in Alzheimer disease.

The immunologic systems of the human being, basically made up of a phagocitary, humoral and cellular system, even when each one of them has differentiated functions, in reality act independently in such a way, that the deficit or depression of one of them will cause functional abnormalities of the others.

On the other hand, the immunological system and the central nervous system (CNS) act in such a way that they possess a two-directional interaction. The immune factors, as for example, the interleukines (IL-1 and IL2) and tumoral necrosis factor (TNT-$\alpha$), have been demonstrated to act on the diverse neurotransmission functions, neuromodulators and conductual factors.

The immune system participates in the ethyopatogeny of some mental disorders, increasing the levels of the interleukin 1. Thus, for example, the interleukin 1 levels increase in patients with a deterioration of the conductual functions and cerebral functions, which indicates that the neuroimmune system is involved in the cognitive processes during old age and in Alzheimer disease.

IL-1$\beta$, IL-2 y, TNLF-$\alpha$ have been identified in the CNS, in which they may act as neurotransmitters, neuromodulators and/or neurotrophic factors. In fact, said cytokines will influence various cerebral functions and conductual processes; and these and other neuroimmune factors may participate in the ethyopatogenia of certain neurodegenerative disorders related to old age as in the case of Alzheimer disease.

In this sense, various high levels of histamine and IL-$\beta$, and reductions of TNF-$\alpha$ have been found in the cerebrum, cephalorachidian liquid, and blood in patients with Alzheimer disease; and it has been observed that the IL-1 promotes the expression of the forunner gene of protein $\beta$ Amiloide (AAP), suggesting that the hyperproduction of APP in patients with Alzheimer disease could be induced by the increase of IL-1. It has also been observed that the serico levels of TNF-$\alpha$ progressivly decrease throughout life, whilst the concentrations of IL-$\beta$ in serum, increases gradually from 25 years of age onwards.

The Meynert (nbM) magnocelular basic core is a structure which provides cholinergic inervation to all the cerebral crust. The destruction of the nbM produces a marked decrease of the cortical cholinergic activity and a deterioration of cognitive functions which imitate the deficits observed in patients with Alzheimer disease. Consequently, animals with injury in their nbM, constitute an acceptable model of the Alzheimer disease.

In the application of European Patent 0503208 is described a procedure for the obtention of a natural hydrosoluble extract, by the extraction of the leaves and/or rhizones of diverse ferns. In this reference to the state of the art, it is expressly specified that said extract presents immunological activities and thus, is of utility in the treatment of disease which deal with or may deal with, suppressor lymphocyte T deficits among which may be quoted: rheumatoid, lupus erythematose, Sjö engren syndrome, type B active chronic hepatitis, Di George syndrome, trombocytopenia, autohemolytic anemia, atopic dermatitis, psoriasis, Basedow disease, Crohn disease, myasthenia gravis, telagiectasia ataxica, vitiligo, alopecia, areata, multiple sclerosis, zoster herpes, etc.

However, said reference does not mention that said natural vegetal extract may be active in the treatment of cognitive and/or neuroimmune dysfunctions.

On the other hand, Spanish Patent 470,204 describes the obtention of a lipidic fraction of natural terpenes, with antipsoriatic activity, by the extraction of the rhizomes and fern leaves. Said terpenes include the fernene and its isomers, as well as other terpenes.

However, said reference does not mention that said lipidic fraction is active in the treatment of cognitive and/or neurodegenerative dysfunctions.

This lipidic fraction is characterized by the presence of Hop-22(29)-eno, identified by the chromatography of gases, using as detector, a mass spectrometer. The major peak of the chromatograms shows fractioning of masses: 410 (19); 395 (10); 191 (100) and 189 (94). Thin coat chromatography shows a stain with Rf of 0,90 being the n-hexane mobile phase and the 60 F254 Silica gel stationary phase, developed with antimonium trichloride in chloroform.

It has now been found that the isolated natural hydrosoluble extract of the rhizome and leaves of ferns Phlebodium decumanum, Polypodium aureum, Polypodium leucotomos, Polypodium vulgate, Polypodium trisereiale, Pteridium aquilinum, Dryopteris crassirhizoma and Cyathea taiwamiana, produces hypoquinesia, improves the production in a training task by passive prevention, and reduces the levels of Il-2 and IL-1$\beta$ in the cerebral crust and the concentration of IL-1$\beta$ in hippocampus, whilst it increases the cortical contents of the tumoralalpha necrosis factor (TNF-$\alpha$) which implies that it has beneficial effects in disorders which deal with cognitive and/or neuroimmune dysfunctions.

Thus, the previously indicated administration of the hydrosoluble vegetal extract, reduces the hyperactivity observed in animals with nbM injuries, standardizing the APM values and increase the power of the cerebral colinergical transmission. Likewise, it was observed that the nbM animals treated more acutely with the extract showed similar training rates to those of control animals, which indicates that the extract re-established the cognitive operational mechanisms.

Said extract tends to standardize the cerebral levels of IL-1$\beta$, IL-2 and TNF-$\alpha$ reducing the hyperproduction of IL-1$\beta$, and IL-2 and increasing the TNF-$\alpha$ content.

The results obtained indicate that the extract possesses nootropic activity (improvement of the conductual alterations) and neuroimmunomodulator effect, and re-establishes the neuroimmunomodulator factors dysfunctions in animals with nbM injuries, which is translated into a neurotrophic action and/or neuroimmunoprotector of the extract.

Continuing with the investigations, it has been found that according to the invention, the immunological activity of said extract also resides in the fraction soluble in alcohol of the same.

Therefore, the present invention provides a pharmaceutical composition with activity in the treatment of cognitive and/or neuroimmune dysfunctions, which include, as active ingredient(s), a natural hydrosoluble extract of rhizomes and/or leaves of: Phlebodiumdecumahum, Polypodiumaureum, Polypodiumleucotomos, Polypodium vulgare, Polypodiumtriseriales, Dryopteris crassirhizoma, Cyathea Taiwaniana and Pteridum Aquilinum, and/or the fraction soluble in alcohol and the fraction liposoluble in said extract.

The liposoluble fraction is obtained in the manner described in Spanish Patent 470,024.

The fraction soluble in alcohol is obtained by means of the following procedure.

Water was added to the hydrosoluble extract described in the application of European Patent 0503208, until a complete solution was accomplished: 500 g of dry base extract were dissolved in i liter of water. The solution was agitated magnetically during 30 minutes attaining limpid, creamy brown coloured solution.

To the solution, was added 4000 ml of methanol, with the appearance of a cream coloured precipitate. The same precipitate appears when using as alcohol, ethanol precipitate and/or isopropanol. The precipitate was separated by filtration and the fraction, soluble in methanol was evaporated at reduced pressure, obtaining a brown coloured caramel, with a production of 40–50% as regards said extract.

This subfraction is characterized by the presence of the following components:

| | |
|---|---|
| Quinic acid | 25%–15% |
| Malic acid | 10%–6% |
| Lactose acid | 12%–5% |
| Citric acid | 5%–3% |
| Fumaric acid | 2%–1% |
| Polysacharides | 17%–8% |

IMMUNOLOGICAL ACTIVITY OF THE FRACTIONS SOLUBLE IN METHANOL

The fraction soluble in methanol and the extract described in the application of European Patent 0503208 were tested in vitro to compare their immunomodulating activity analysing the proliferation of mononuclear cells of peripherical blood (PBL) of 10 healthy controls, obtained by centrifugation in density gradient.

The cells were sown three times in sheets of 96 flat bottomed cups, at a proportion of 250.000 PBL/cup. The stimulation was carried out on one hand with phythohemoglobutyne (PHA) and pokeweed (PWM) to which was added the extract described in the application of European Patent 0503208 at different dosages, and on the other hand with the single extract. In both, the dosages of extract used were of 75, 150, 500, 1000, 1500, 4500 µg/ml. The results obtained were the following:

—When the extract was added to the PHA or to the PWM, a slight increase of the proliferation was observed in some of the patients at an extract dosage of 75–150 µg/ml, and a slight decrease of the same high dosage (1500–4500 µg/ml). However, analysing the group as a whole, no statistically significant effect was found.

—When the effect of the lynphocyte proliferation on the single extract was analysed, it was found that at low dosage (75–150 µg/ml), it was capable of stimulating the proliferation, whilst at high dosage (>1.500 µg/ml) it suppressed it.

| Cells without stimulation | Cells stimulated with extract | | |
|---|---|---|---|
| 0 | 75 | 150 | 4,500 |
| 3,800 cpm | 5,800 cpm | 7,000 cpm | 3,100 cpm |

With dosages of 150 µg/ml of extract, an 85% increase of the proliferation was observed in relation to the cells without stimulation (p=0.01). At higher dosages of extract (4,500 µg/ml), the proliferation drops once again, to even below the quantities observed in the cells without stimulation. If the stimulation with 150 µg/ml of extract (maximum stimulation) is compared with the one observed when stimulating with 4,500 µg/ml, the decrease produced in the proliferation is almost of 60% (P=0.02).

—When the fraction soluble in alchohol obtained from the extract described in the application of European Patent 0503208 was tested, the following results were obtained.

—When added to the PHA, only a suppressor effect of the proliferation with high dosage of the fraction soluble in alcohol (4500 µg/ml) was observed.

| Cells stimulated with PHA | Cells stimulated with PHA + 4,500 µg/ml of fraction |
|---|---|
| 7,714 c | 1,782 cpm p < 0.001 |

—When the fraction was tested alone, similar results were observed to the results obtained with the extract described in the application of European Patent 0503208, that is to say, there was an increase in the proliferation at low dosages of the fraction product, soluble in methanol (75–150 µg/ml), though much greater than the one observed with the extract described in the application of European Patent 0503208 and a decrease of the proliferation at high dosages (4,500 µg/ml)

| Cells without stimulation | Cells stimulated with the fraction | | |
|---|---|---|---|
| 0 | 75 | 150 | 4,500 |
| | 1,956 cpm | 2,500 cpm | 118 cpm |

Between 0 and 75–150 p=0.005
Between 75–150 and 4,500 p<0.001

From the previous results is deduced that the immunomodulator activity of the extract obtained in the application of European Patent 0503208 lies on the fraction soluble in alcohol.

CLINICAL STUDIES

A study has been conducted of the neuroprotection effect of the pharmaceutical composition of the invention with the following composition:

| | |
|---|---|
| Hydrosoluble extract Equivalent 60 mg of fraction soluble in alcohol | 118 mg |
| Lipidic fraction | 2 mg |
| Starch | 100 mg |
| Talcum powder | 115 mg |

| | |
|---|---|
| Magnesium stearate | 10 mg |
| Aerosil 200 | 1 mg | on Alzheimer disease as a paliative, assisting treatment. An open pilot study has been conducted giving the said pharmaceutical composition formulation to patients with Alzheimer disease and vascular dementia in combination with a therapeutical triad (multifactorial) composed of CDP-choline (100 mg/day) Piracetam [4 g/day (tid)] and Nimodipine (30–90 mg/day, tid).

Material and Methods

In the present study, 24 patients were included with an Alzheimer disease diagnosis (AD) and vascular dementia (DV), divided into 4 groups of 6 patients each; group 1 (G1), (Ad, n=6, age=60.83±4.16 years, range=55–65 years), group 2 (G2): (Ad, n=6, age=61,000±4.04 years, range=54–65 years), group 3 (G3): (VD, n=6, age=73.50±5.92, range= 66–80 years), group 4 (G4) (VD, n=6, age=73.16±4.95, range=66–80 years).

The diagnosis criteria were those of the DSMIII-R and of the NINCDS-ADRDA.

The evaluated parameters were: neuropsychological evaluation, cognitive and non-cognitive, with special attention to the Alzheimer's Disease Scale Assessment (ADAS) and Mini-Metal State Examination (MMSE), cerebral bioelectrical activity measured with the conventional EEG and the Cerebrum Cartography (CC): cerebral hemodynamic function of the left and right, middle cerebral arteries (MCA-L, MCA, R) and of the basilar artery (BA) using the Doppler Transcraneal (TCD) ultrasonography; and the tolerance by means of clinical interview and laboratory tests, evaluated during the inclusion visit in the study and after 3 months of multifactorial therapy.

All the patients were treated with the association of CDP-Choline (1000 mg/day/b.v./3 months), Piracetam (4,000 mg/day/b.v./3 months) and Nimodipine (60 mg/day/b.v./3 months). Besides groups G2 and G4, they received (360 mg/day/b.v./3 months).

The statistical analysis was carried out using student's "t" for matched data and the analysis of the variance (ANOVA).

BV: Basic Visit
V1: Intermediate Visit (1 month)
V3: Final visit of the study
ADASTS: Total Puntuation of the ADAS
ADASCB: Cognitive Scale of the ADAS
MMSE: Mini-Metal State Examination
EPR: Effective Pulsation Range
MCA-L: Middle Cerebral Left Artery
MCA-R: Middle Cerebral Right Artery
BA: Basilar Artery

RESULTS

* ADAS Test

The neuropsychological evaluation showed a positive reply to groups G2 and G4 in the cognitive production after 3 months of multifactorial therapy.

* MMSE Test

The total puntuation in the MMSE showed a tendency to an increase of the puntuation in the group G2 (group treated with the composition), less deterioration whilst the other groups remained stable throughout the study.

Cerebral Bioelectrical Activity

The study of the cerebral bioelectrical activity evaluated by means of the quantitative EEG showed a significant increase of the alpha activity in the right hemisphere (T4) after 3 months of therapy in group G2.

These results are interpreted as an acceleration of the cerebral bioelectric activity after treatment with the pharmaceutical composition under study.

In patients of group G4, a significant increase was observed in the theta activity in FP1 and F3 accompanied by a tendency to a decrease of delta activity. Additionally, a significant decrease was observed of delta activity in Cz associated to a tendency of increase of the theta rythm. These findings could be interpreted similarly as a "relative" acceleration of the cerebral bioelectrical activity.

Cerebral Hemodynamic Study

Cerebral hemodynamic function.

The cerebral hemodynamicas is evaluated fundamentally through effective pulsation range (EPR) flow peripherical resistance rate. A high EPR indicates low flow resistance and viceversa. The results of the cerebral hemodynamic function showed a tendency to an increase of the EPR in the middle cerebral arteries (MCAR), right, and (MCA-L) left, of groups G2, G3 and G4, with a tendency to a decrease of the EPR in G1. In the basilar artery, a significant increase of the EPR was observed in AD patients treated with (G2), with a similar tendency in groups G3 and G4 and a tendency to decrease of the EPR in G1.

* Tolerance

No negative or deviatory effects of the reference parameters were observed in the blood and hemogramme biochemistry.

SUMMARY

1. The neuro-psychological evaluation has demonstrated a positive reply of groups G2 and G4 in cognitive production after 3 months of multifactorial therapy.

2. The cerebral bioelectrical activity of the patients included in G2 and G4 showed a tendency to attenuation of the slow frequencies and a tendency to activation of rapid frequencies.

3. A tendency to decrease of the periperical resistances was observed in groups G2, G3 and G4 at the end of the study.

4. A suitable therapeutical tolerance was observed evaluated by means of clinical examination and laboratory tests.

With this strategy, we have been capable of checking that the group treated with the pharmaceutical composition of the invention plus the triad CDPC+PRC+NDP responded better than the group treated with CDPC+PRC+NDP, this evidence being confirmed at psychometric. electrophysiological (cerebral cartography) and hemodynamic (Dopple transcraneal ultrasonography) level. In the group of the pharmaceutical composition of the invention, secondary effects other than those found in the group CDPC+PRC+NDP were not discovered, which reinforces the therapeutical safety and tolerability of our product.

The data of the present study give evidence that the neuroimmune-regulatory therapy with the pharmaceutical composition of the invention may contribute to the ethyopatogenic treatment of senile dementia.

The pharmaceutical compositions of this invention, contain the active substance in unitary administration dosages of 40 mg, 120 mg and 240 mg, the minimum active dosage being 80 mg and the maximum of 1,200 mg, to remove the existing differences between age and weight of the patients and the processes to be treated, which will sometimes be acute and of short duration and at other times will be chronic and of long duration.

Given the practical atoxicity, tolerance, lack of secondarisms and good gastricoduodenum absorption, the preferred manner of administration is orally, in dosages of active subtances, variable according to description, between 80 mg and 1,200 mg distributed in 2–3 preprandial daily doses, with a time distribution as equitable as possible, in such a way that the concentrations in the blood stream maintain a stable and continued immulological activity level.

The composition of the present invention may be useful in diverse pharmaceutical forms for its dosification, such as:

Tablets, capsules: the product shall be granulated to accomplish this, with suitable excipients and be conditioned for subsequent preparation of unitary dosages of capsules or tablets.

Customary excipients in this preparation are, lactase, starch, talcum powder, magnesium stearate, Aerosil and other similar products.

| Raw material | Quantities per capsule | Quantities per lot 100,000 caps. |
|---|---|---|
| Hydrosoluble extract | 118 mg | 12,0 kg |
| Lipidic fraction | 2 mg | |
| Starch | 100 mg | 10,0 kg |
| Lactose | 150 mg | 15,0 kg |
| Talcum Powder | 115 mg | 11,5 kg |
| Stearate of mg | 10 mg | 1,0 kg |
| Aerosil 200 | 1 mg | 0,1 kg |

Firstly, mix the hydrosoluble extract with the lipidic fraction, the starch and the lactose, granulate, dry and grind them, passing them through a sieve for their subsequent blending with the rest of the excipients and dosificate at 496 mg/capsule.

We claim:

1. A method of producing a neuroprotective effect in a patient in need thereof by administering a neuroprotective effective amount of a pharmaceutical composition into the patient, utilizing a pharmaceutical composition for the treatment of cognitive, neurodegenerative or neuroimmune dysfunction disorders containing a neuroprotective effective amount of an active ingredient and an acceptable pharmaceutical vehicle, in which the active agent comprises an isolated, natural hydrosoluble extract of the rhizome or leaves of Phlebodium decumanum, Polypodium aereum, Polypodium leucotomos, Polypodium vulgare, Polypodium trisereiale, Pteridium aquilinum, Dryopteris crassirhizoma and Cyathea taiwamiana.

2. A method of claim 1, in which the amount of extract administered is between 800 and 1,200 mg per day.

3. A method of claim 2, in which the amount of extract is administered in the form of two or three time separated doses.

4. A method of claim 1, in which the administration is oral.

5. A method of producing a neuroprotective effect to a patient in need thereof by administering a neuroprotective effective amount of a pharmaceutical composition into the patient, utilizing the pharmaceutical composition for the treatment of cognitive, neurodeqenerative or neuroimmune dysfunction disorders containing a neuroprotective effective amount of an active ingredient and an acceptable pharmaceutical vehicle, in which the active agent comprises an alcohol soluble, isolated, natural hydrosoluble extract of the rhizome or leaves of Phlebodium decumanum, Polypodium aereum, Polypodium leucotomos, Polypodium vulgate, Polypodium trisereiale, Pteridium aquilinum, Dryopteris crassirhizoma and Cyathea taiwamiana.

6. A method of claim 5, in which the amount of extract administered is between 800 to 1,200 mg per day.

7. A method of claim 5, in which the amount of extract is administered in the form of two or three time separated doses.

8. A method of claim 5, in which the administration is oral.

* * * * *

UNITED STATES PATENT AND TRADEMARK OFFICE
CERTIFICATE OF CORRECTION

PATENT NO. : 5,601,829
DATED : February 11, 1997
INVENTOR(S) : Quintanilla Almagro et al.

It is certified that error appears in the above-identified patent and that said Letters Patent is hereby corrected as shown below:

Column 8, line 17, for "800", read --80--; and line 39 for "800" read --80--.

Signed and Sealed this

Twenty-ninth Day of May, 2001

Attest:

NICHOLAS P. GODICI

*Attesting Officer*  *Acting Director of the United States Patent and Trademark Office*